United States Patent [19]

Hartmann et al.

[11] Patent Number: 4,459,304
[45] Date of Patent: Jul. 10, 1984

[54] COMBATING PESTS WITH 2-ANILINO-3,5-DINITRO-BENZOTRIFLUO-RIDES

[75] Inventors: Alfons Hartmann, Beckingen; Erich Klauke, Odenthal; Ingeborg Hammann, Cologne; Peter Roessler, Bergisch-Gladbach; Volker Paul, Solingen, all of Fed. Rep. of Germany

[73] Assignee: Bayer Aktiengesellschaft, Leverkusen, Fed. Rep. of Germany

[21] Appl. No.: 24,845

[22] Filed: Mar. 28, 1979

Related U.S. Application Data

[63] Continuation of Ser. No. 911,590, Jun. 1, 1978, abandoned.

[30] Foreign Application Priority Data

Jun. 24, 1977 [DE] Fed. Rep. of Germany ....... 2728536

[51] Int. Cl.³ .............. A61K 31/335; A61K 31/135; C07C 87/60
[52] U.S. Cl. ............................. 424/278; 260/465 E; 549/365; 564/433; 424/304; 424/330
[58] Field of Search ............. 260/340.3, 577, 574, 260/465 E; 424/330, 278, 304; 549/365; 564/433

[56] References Cited

U.S. PATENT DOCUMENTS

| | | | |
|---|---|---|---|
| 3,257,190 | 6/1966 | Soper | 260/577 X |
| 3,332,769 | 7/1967 | Soper | 260/577 X |
| 3,403,180 | 9/1968 | Soper | 260/577 |
| 3,442,639 | 5/1969 | Soper | 260/577 X |
| 3,716,585 | 2/1973 | Strong et al. | 260/577 X |
| 3,950,377 | 4/1976 | Barlow | 260/465 E |
| 4,041,172 | 8/1977 | Barlow | 424/304 |
| 4,117,167 | 9/1978 | Barlow | 424/330 |
| 4,128,665 | 12/1978 | Hunt et al. | 424/304 |
| 4,215,145 | 7/1980 | Grantham | 424/324 X |

FOREIGN PATENT DOCUMENTS

| | | | |
|---|---|---|---|
| 2509416 | 3/1975 | Fed. Rep. of Germany | 260/577 |
| 1455207 | 11/1976 | United Kingdom | 564/433 |

*Primary Examiner*—Ethel G. Love
*Attorney, Agent, or Firm*—Sprung, Horn, Kramer & Woods

[57] ABSTRACT

2-Anilino-3,5-dinitro-benzotrifluorides of the formula

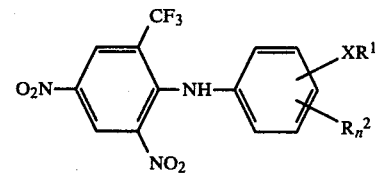

in which
X is O, S, SO or $SO_2$,
n is 1, 2, 3 or 4,
$R^1$ is haloalkyl, haloalkoxyalkyl, phenyl, halophenyl, haloalkylphenyl, haloalkoxyphenyl, haloalkylmercaptophenyl or haloalkylsulphonyl, and
$R^2$ each independently is hydrogen, halogen, cyano, nitro, alkyl, haloalkyl or haloalkoxyalkyl, or
$XR^1$ and $R^2$, when in the ortho-position relative to one another, together with the two adjacent carbon atoms of the phenyl nucleus, form an optionally halogen-substituted dioxanyl ring, or
provided X represents S, SO or $SO_2$, $R^1$ can represent unsubstituted alkyl in addition to the aforementioned radicals, which possess arthropodicidal, nematicidal, fungicidal and bactericidal properties.

14 Claims, No Drawings

COMBATING PESTS WITH 2-ANILINO-3,5-DINITRO-BENZOTRIFLUORIDES

This is a continuation of application Ser. No. 911,590, filed June 1, 1978, now abandoned.

The present invention relates to and has for its objects the provision of particular new 2-anilino-3,5-dinitro-benzotrifluorides which possess pesticidal properties, active compositions in the form of mixtures of such compounds with solid and liquid dispersible carrier vehicles, and methods for producing such compounds and for using such compounds in a new way especially for combating pests, e.g. arthropods, nematodes, fungi and bacteria, with other and further objects becoming apparent from a study of the within specification and accompanying examples.

Certain 2-arylamino-3,5-dinitro-benzotrifluorides having insecticidal, acaricidal, fungicidal and bactericidal properties have already been disclosed (see German Offenlegungsschrift (German Published Specification) No. 2,509,416). However, their action is not completely satisfactory, above all when low concentrations are used.

The present invention now provides, as new compounds, the 2-arylamino-3,5-dinitro-benzotrifluorides of the general formula

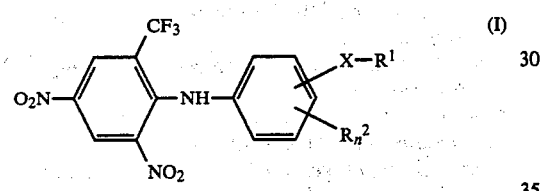

in which
X represents O, S, SO or $SO_2$,
n represents 1, 2, 3 or 4,
$R^1$ represents alkyl which is substituted by halogen and/or by halogenoalkoxy or represents phenyl which is optionally substituted by halogen, halogenoalkyl, halogenoalkoxy, halogenoalkylmercapto or halogenoalkylsulphonyl and
$R^2$ represents hydrogen, halogen, cyano, nitro or alkyl which is optionally substituted by halogen and/or by halogenoalkoxy, each $R^2$ being selected independently when n is 2, 3 or 4, or
$XR^1$ and $R^2$, when in the ortho-position relative to one another, together with the two adjacent carbon atoms of the phenyl nucleus, can form an optionally halogen-substituted dioxanyl ring or
provided X represents S, SO or $SO_2$, $R^1$ can represent unsubstituted alkyl, as an alternative to the radicals mentioned above.

Surprisingly, the 2-arylamino-3,5-dinitro-benzotrifluorides of the formula (I) exhibit a higher insecticidal, acaricidal, development-inhibiting, fungicidal and bactericidal potency than the compounds known from German Offenlegungsschrift No. 2,509,416, which are closely related chemically and have the same type of action. The substances according to the invention thus represent an enrichment of the art.

Preferably, in formula (I), X represents O, S or $SO_2$, and the various alkyl and alkoxy moieties have up to 4 carbon atoms. Preferably $R^1$ represents alkyl with 1 to 4 carbon atoms, halogenoalkyl with 1 to 4 carbon atoms or phenyl which is optionally substituted by chlorine or by trifluoromethylsulphonyl. $R^2$ represents hydrogen, halogen or trifluoromethyl and n represents 1 or 2, or $X-R^1$ and $R^2$ form a 1,3-dioxane ring which is substituted by fluorine and fused to the phenyl nucleus.

Compounds of the general formula (I) in which X represents O, S or $SO_2$, $R^1$ represents methyl, ethyl, trifluoromethyl or phenyl which is optionally substituted by chlorine or trifluoromethylsulphonyl, $R^2$ represents hydrogen, chlorine or trifluoromethyl and n represents 1, or in which $X-R^1$ and $R^2$ form a 1,3-dioxane ring which is substituted by fluorine and fused to the phenyl nucleus, are particularly preferred.

The invention also provides a process for the preparation of a 2-arylamino-3,5-dinitro-benzotrifluoride of the formula (I), in which (a) an aniline of the general formula

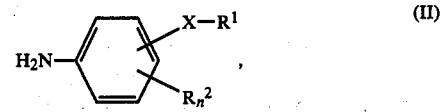

in which X, $R^1$, $R^2$ and n have the meanings stated above, is reacted with 2-chloro-3,5-dinitro-benzotrifluoride, of the formula

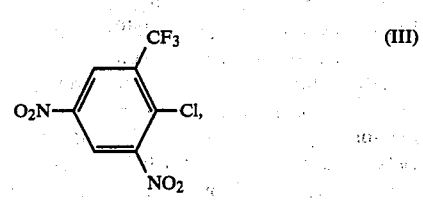

in the presence of an acid-binding agent, and optionally in the presence of a diluent, or (b) 2-amino-3,5-dinitro-benzotrifluoride, of the formula

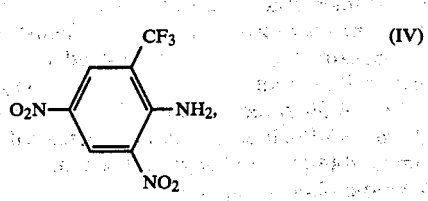

is reacted with a compound of the general formula

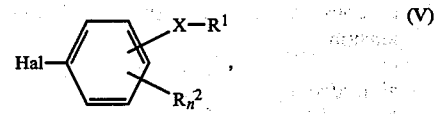

in which
X, $R^1$, $R^2$ and n have the meanings stated above and
Hal represents fluorine, chlorine or bromine, in the presence of an acid-binding agent, and optionally in the presence of a diluent, or (c) a compound of the general formula (I) which has been prepared according to process variant (a) or (b) and in which $R^1$, $R^2$ and n have the meanings stated above and X represents S, is converted with the aid of an oxidizing agent, optionally in the presence of a diluent, into the corresponding compound of the formula (I) in which X represents SO or $SO_2$.

If 2-chloro-3,5-dinitro-benzotrifluoride and 4-trifluoromethoxy-aniline are used as starting materials, the course of the reaction can be represented by the following equation:

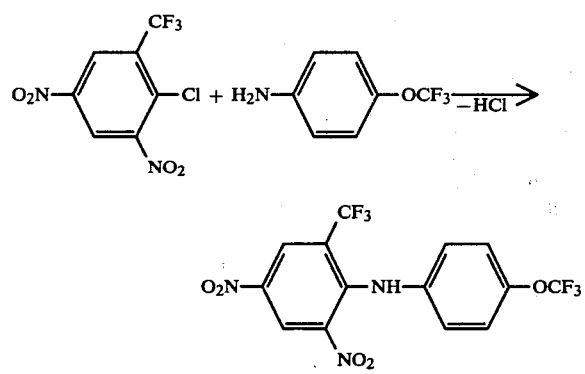

Compounds of the formulae (II), (III), (IV) and (V) to be used as starting materials are known and can be prepared by known processes.

Examples of anilines of the formula (II) which can be used in process variant (a) - which is the preferred process variant - are: 2-trifluoromethoxy-aniline, 3-trifluoromethoxy-aniline, 4-trifluoromethoxy-aniline, 2-chloro-4-trifluoromethoxy-aniline, 3-chloro-4-trifluoromethoxy-aniline, 2-trifluoromethylmercapto-aniline, 3-trifluoromethylmercapto-aniline, 4-trifluoromethylmercapto-aniline, 2-chloro-5-trifluoromethylmercapto-aniline, 3-chloro-4-trifluoromethylmercapto-aniline, 3-chloro-4-chlorodifluoromethylmercapto-aniline, 4-methylsulphonyl-aniline, 4-trifluoromethylsulphonyl-aniline, 2-chloro-4-trifluoromethylsulphonyl-aniline, 2-chloro-5-trifluoromethylsulphonyl-aniline, 2,6-dichloro-4-trifluoromethylsulphonyl-aniline, 6-amino-2,2,4,4-tetrafluoro-1,3-benzodioxane, 2-amino-5-methylmercapto-benzotrifluoride, 3-amino-4-methylmercapto-benzotrifluoride, 2-amino-5-methylsulphonyl-benzotrifluoride, 3-amino-4-ethylsulphonyl-benzotrifluoride, 5-amino-2-(4-chlorophenoxy)-benzotrifluoride, 4-(4-trifluoromethylsulphonyl-phenoxy)-aniline, 2-amino-5-(4-chlorophenylthio)-benzotrifluoride, 3-amino-4-(4-chlorophenylthio)-benzotrifluoride and 2-amino-diphenyl sulphone.

Suitable diluents for process variants (a) and (b) are inert organic solvents. Dimethylformamide or tetrahydrofuran are preferably used. It is sometimes also advantageous to carry out the reaction in an aqueous suspension.

Suitable acid-binding agents are bases, such as alkali metal hydroxides, carbonates or hydrides or alkaline earth metal hydroxides, carbonates or hydrides. Potassium hydroxide, sodium hydride or sodium hydrogen carbonate are preferably used.

The reaction temperatures in process variant (a) and (b) can be varied within a relatively wide range. In general, the reaction is carried out between $-10°$ and $+150°$ C., preferably at from 10° to 40° C., when an organic solvent is used, and at 100° C. when the reaction is carried out in an aqueous suspension. In the latter case, the temperature can be further increased by using a pressure vessel.

The reactants are usually employed in equimolar amounts, but it is also possible to use either of the components in excess.

In carrying out process variant (c) glacial acetic acid is preferably employed as the solvent and hydrogen peroxide is preferably used as the oxidizing agent. For the preparation of the sulphoxides, the reaction is carried out with equimolar amounts, preferably at 10°–30° C., and for the preparation of the sulphones, the reaction is carried out with at least twice the molar amount of hydrogen peroxide, preferably at the boiling point of the solvent.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The abovementioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera* spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips Tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Litho colletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *La-*

*phygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Liptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolonthia, Amphimallon solstitialis* and *Costelytra zealandica;* from the order of the Hymenoptera, for example Diprion spp., Hoplocampa spp., Lasius spp., Monomorium pharaonis and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp..

The plant-parasitic nematodes include Pratylenchus spp., *Radopholus similis, Ditylenchus dipsaci, Tylenchulus semipenetrans,* Heterodera spp., Meloidogyne spp., Aphelenchoides spp., Longidorus spp., Xiphinema spp., and Trichodorus spp..

The active compounds according to the invention exhibit a powerful fungitoxic action and bacteriotoxic action. They do not damage crop plants in the concentrations required for combating fungi and bacteria. For these reasons, they are suitable for use as plant protection agents for combating fungi and bacteria. Fungitoxic agents are employed in plant protection for combating Plasmodiophoromycetes, Oomycetes, Chytridiomycetes, Zygomycetes, Ascomycetes, Basidiomycetes and Deuteromycetes.

The active compounds according to the invention have a broad spectrum of action and can be used against parasitic fungi which attack above-ground parts of plants or which attack the plants through the soil, as well as against seed-borne pathogens.

The compounds according to the invention act against fungi and bacteria which attack various crop plants, such as, for example, species of Phythium, species of Phytophthora, species of Fusarium, *Verticillium alboatrum, Phialophora cinerescens, Sclerotinia sclerotiorum,* species of Botrytis, *Cochliobolus miyabeanus, Mycosphaerella musicola, Cercospora personata, Helminthosporium gramineum,* species of Alternaria, species of Colletotrichum, *Venturia inaequalis,* species of Rhizoctonia, *Thielaviopsis basicola, Xanthomonas oryzae* and *Pseudomonas lachrymans.* The compounds according to the invention act both against cereal diseases, such as, for example, *Puccinia recondita, Erysiphe graminis* and *Tilletia caries* and against rice diseases, such as, for example, *Pyricularia oryzae* and *Pellicularia sasakii.*

The active compound can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid solvents diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

Especially when used as leaf fungicides, the active compound concentrations in the use forms can be varied within a fairly wide range. They are, in general, from 0.1 to 0.00001 percent by weight, preferably from 0.05 to 0.0001 percent.

For the treatment of seed, amounts of active compound of 0.001 to 50 g, preferably 0.01 to 10 g, are in general employed per kilogram of seed.

For the treatment of soil, amounts of active compound of 1 to 1,000 g, preferably of 10 to 200 g, are generally employed per cubic meter of soil.

The present invention also provides arthropodicidal, nematicidal, fungicidal or bactericidal compositions containing as active ingredient a compound of the present invention in admixture with a solid or liquefied gaseous diluent or carrier or in admixture with a liquid diluent or carrier containing a surface-active agent.

The present invention also provides a method of combating arthropods (especially insects or acarids), nematodes, fungi or bacteria which comprises applying to the arthropods, nematodes, fungi or bacteria, or to a habitat thereof, a compound of the present invention alone or in the form of a composition containing as active ingredient a compound of the present invention in admixture with a diluent or carrier.

The present invention further provides crops protected from damage by arthropods, nematodes, fungi or bacteria by being grown in areas in which immediately prior to and/or during the time of the growing a compound of the present invention was applied alone or in admixture with a diluent or carrier.

It will be seen that the usual methods of providing a harvested crop may be improved by the present invention.

EXAMPLE 1

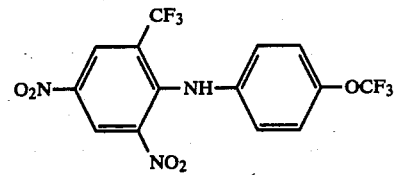

A suspension of 27.0 g (0.1 mol) of 2-chloro-3,5-dinitro-benzotrifluoride and 17.7 g (0.1 mol) of 4-trifluoromethoxy-aniline in 200 ml of water was heated to the boil. 9.3 g (0.11 mol) of sodium bicarbonate were introduced in the course of 30 minutes and the mixture was heated under reflux for a further 2 hours. It was left overnight at room temperature, whereupon a yellow, crystalline solid separated out. After filtering off and washing with petroleum ether, 36.8 g of 2-(4-trifluoromethoxy-anilino)-3,5-dinitro-benzotrifluoride of melting point 104° C. were obtained.

The following compounds were obtained analogously:

TABLE 1

(VI) structure: O$_2$N—(aryl with CF$_3$)—NH—Ar, with NO$_2$

| Compound | Ar | Melting point (°C.) |
|---|---|---|
| 2 | phenyl-O-CF$_2$-O (difluoromethylenedioxy-phenyl, with F's) | 125 |
| 3 | 2-CF$_3$-phenyl-O-(4-Cl-phenyl) | 174 |
| 4 | 4-SCF$_3$-phenyl | 108 |
| 5 | phenyl-O-(4-SO$_2$CF$_3$-phenyl) | 138 |

EXAMPLE 2

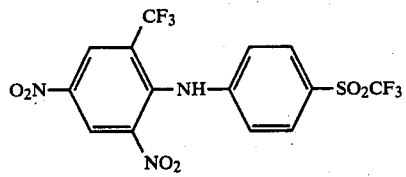
(6)

5.6 g (100 mmol) of powdered potassium hydroxide were added in portions to a solution of 11.2 g (50 mmol) of 4-trifluoromethylsulphonyl-aniline in 100 ml of dry dimethylformamide at room temperature. A solution of 13.6 g (50 mmol) of 2-chloro-3,5-dinitrobenzotrifluoride in 80 ml of dry dimethylformamide was then added dropwise at 25° C. The mixture was stirred overnight at room temperature and filtered, 100 ml of glacial acetic acid were added to the filtrate and the mixture was discharged onto ice. 11.5 g of 2-(4-trifluoromethylsulphonyl-anilino)-3,5-dinitrobenzotrifluoride were filtered off in the form of yellow crystals. Melting point 172° C.

The following compounds were obtained analogously:

TABLE 2

Structure (VI): 2-NO2, 4-O2N, 6-CF3 phenyl with NH—Ar

| Compound | Ar | Melting point (°C.) |
|---|---|---|
| 7 | 4-(SO2CF3)-2-Cl-phenyl | 157–158 |
| 8 | 3,5-dichloro-4-(SO2CF3)-phenyl | 125 |
| 9 | 2-Cl-4-(OCF3)-phenyl | ($n_D^{20}$ 1.576) |
| 10 | 3-CF3-4-(SCH3)-phenyl | 115 |
| 11 | 3-CF3-4-(SO2—CH3)-phenyl | 192 |
| 12 | 3-CF3-5-(SO2—C2H5)-phenyl | 176 |

EXAMPLE 3

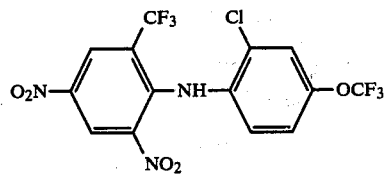
(13)

A solution of 21.2 g (0.1 mol) of 2-chloro-4-trifluoromethoxy-aniline in 200 ml of dimethylformamide was added to a suspension of 5 g of sodium hydride (coated with 20% of paraffin) in 100 ml of dry dimethylformamide at 0° C. The mixture was stirred at 25° C. for 1 hour and cooled to 10° C. and a solution of 27.1 g (0.1 mol) of 2-chloro-3,5-dintro-benzotrifluoride in 250 ml of dimethylformamide was added dropwise. After standing overnight, the mixture was filtered, 500 ml of glacial acetic acid were added to the filtrate and the reaction mixture was poured onto ice, whereupon a dark oil separated out. It was separated off and freed from solvent residues in vacuo. 35.4 g of 2-(2-chloro-4-trifluoromethoxy-anilino)-3,5-dinitro-benzotrifluoride were thus obtained as a viscous mass; $n_D^{20} = 1.574$.

The following compounds could be prepared in a similar manner:

TABLE 3

Structure (VI): 2-NO2, 4-O2N, 6-CF3 phenyl with NH—Ar

| Compound | Ar | Melting point (°C.) |
|---|---|---|
| 14 | 2-Cl-4-(SO2CF3)-phenyl | 110 |
| 15 | 2-SCH3-4-CF3-phenyl | 140 |
| 16 | 2-CF3-4-(S-4-Cl-phenyl)-phenyl | 104 |
| 17 | 2-CF3-4-(S-4-Cl-phenyl)-phenyl | 124 |
| 18 | 4-(SO2—CH3)-phenyl | 172 |

TABLE 3-continued (VI) $O_2N\text{-}C_6H_2(CF_3)(NO_2)\text{-}NH\text{-}Ar$

| Compound | Ar | Melting point (°C.) |
|---|---|---|
| 19 | phenyl-SO$_2$-phenyl | 114 |
| 20 | 2-Cl, 4-SCF$_3$-phenyl | dark, viscous oil |
| 21 | 4-SCF$_3$-cyclohexyl | 95 |
| 22 | 3-SCF$_3$, 4-Cl-phenyl | ($n_D^{20}$ = 1.574) |
| 23 | 2-OCF$_3$-phenyl | — |
| 24 | 3-OCF$_3$-phenyl | 114 |
| 25 | 3-SCF$_3$-phenyl | 78–79 |

EXAMPLE 4

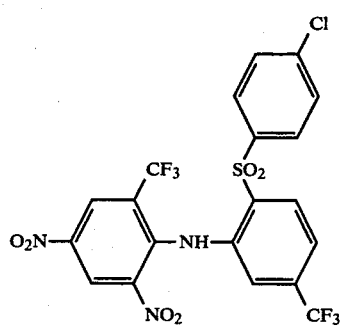

(26)

3 ml of 35% strength hydrogen peroxide were added to 5.4 g (10 mmol) of 2-[2-(4-chlorophenylthio)-5-trifluoromethyl-anilino]-3,5-dinitro-benzotrifluoride (see compound #17) in 100 ml of glacial acetic acid and the mixture was heated under reflux for 3 minutes. After cooling, it was poured into 1 liter of ice-water. The crystals of 2-[2-(4-chlorophenylsulphonyl)-5-trifluoromethyl-anilino]-3,5-dinitro-benzotrifluoride were filtered off and washed with water and petroleum ether. Yield 5.6 g; melting point 191° C.

EXAMPLE 5

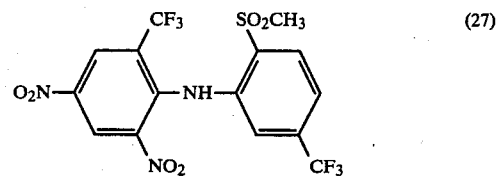

(27)

Compound 15 prepared according to Example 3, when treated in a manner similar to that described in Example 4, gave the compound of the above formula; melting point 185° C.

The pesticidal activity of the compounds of this invention is illustrated by the following biotest examples wherein the compounds according to the present invention are each identified by the number (given in brackets) from the preparative examples, hereinabove.

The known comparison compounds are identified as follows:

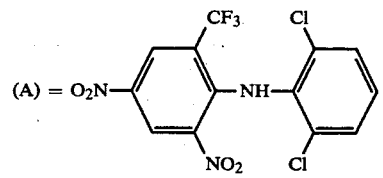

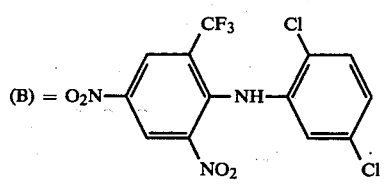

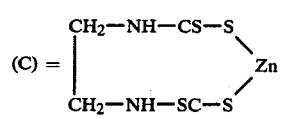

EXAMPLE 6

Tetranychus test (resistant)

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent and the stated amount of emulsifier and the concentrate was diluted with water to the desired concentration.

Bean plants (*Phaseolus vulgaris*) which were heavily infested with the two-spotted spider mite (*Tetranychus urticae*) in all stages of development were sprayed with the preparation of the active compound until dripping wet.

After the specified periods of time, the degree of destruction was determined as a percentage: 100% meant that all of the spider mites were killed whereas 0% meant that none of the spider mites were killed.

The active compounds, the concentrations of the active compounds, the evaluation times and the results can be seen from the following table:

TABLE 4

| Active compounds | (mites which damage plants) Tetranychus test | |
|---|---|---|
| | Active Compound concentration in % | Degree of destruction in % after 2 days |
| (A) | 0.001 | 98 |
| | 0.0001 | 0 |
| (21) | 0.001 | 100 |
| | 0.0001 | 50 |
| (4) | 0.001 | 100 |
| | 0.0001 | 99 |
| (10) | 0.001 | 98 |
| | 0.0001 | 50 |
| (1) | 0.001 | 100 |
| | 0.0001 | 70 |
| (13) | 0.001 | 100 |
| | 0.0001 | 100 |
| (9) | 0.001 | 100 |
| | 0.0001 | 100 |
| (2) | 0.001 | 100 |
| | 0.0001 | 100 |
| (24) | 0.001 | 100 |
| | 0.0001 | 95 |
| (25) | 0.001 | 100 |
| | 0.0001 | 95 |
| (22) | 0.001 | 100 |

EXAMPLE 7

Phaedon larvae test

Solvent: 3 parts by weight of dimethylformamide
Emulsifier: 1 part by weight of alkylarly polyglycol ether To produce a suitable preparation of active compound, 1 part by weight of the active compound was mixed with the stated amount of solvent containing the stated amount of emulsifier and the concentrate was diluted with water to the desired concentration.

Cabbage leaves (*Brassica oleracea*) were sprayed with the preparation of the active compound until dripping wet and were then infested with mustard beetle larvae (*Phaedon cochleariae*).

After the specified periods of time, the degree of destruction was determined in %: 100% meant that all of the beetle larvae had been killed whereas 0% meant that none of the beetle larvae had been killed.

The active compounds, the concentrations of the active compounds, the evaluation times and the results can be seen from the following table:

TABLE 5

| Active compounds | (insects which damage plants) Phaedon larvae test | |
|---|---|---|
| | Active compound concentration in % | Degree of destruction in % after 3 days |
| (B) | 0.01 | 100 |
| | 0.001 | 0 |
| (4) | 0.01 | 100 |
| | 0.001 | 50 |
| (13) | 0.01 | 100 |
| | 0.001 | 85 |
| (14) | 0.01 | 100 |
| | 0.001 | 80 |

Examples 8 and 9, which are given below, show the arthropod development-inhibiting action of the compounds according to the invention without implying a limitation in respect of the breadth of action of these compounds. In the experiments, the morphological changes, such as half-pupated insects, incompletely slipped larvae or caterpillars, defective wings, pupal cuticula in the case of imagos and the like are rated as malformations over the entire stated development of the test insects. The sum of the morphological malformations, together with the insects killed during the sloughing or the metamorphosis, is given in percent of the test insects.

EXAMPLE 8

Development-inhibiting action

Test insect: *Laphygma exempta* (eggs)
Feed: corn (*Zea mays*)
Solvent: 10 parts by weight of acetone
Emulsifier: 1 part by weight of alkylaryl polyglycol ether To produce a suitable preparation of active compound, 2 parts by weight of active compound were mixed with the stated amount of solvent, emulsifier and sufficient water to produce a 1% strength mixture, which was diluted with water to the desired concentration.

Deposited eggs, at the rate of 30 eggs on a filter-paper, were moistened with 1 ml of active compound solution of the stated concentration in ppm (parts per million) and were observed, in plastic boxes, until the young larvae slipped. The young larvae were fed with corn leaves which had been sprayed with the stated concentration of active compound solution on the same day as the eggs.

The development of the test insects was observed up to the larvae of the third stage.

As a control, deposited eggs were treated in the same manner with solvent and emulsifier of the corresponding concentration, and feeding was carried out with corn leaves. The results can be seen from the following table.

TABLE 6

| | Development-inhibiting action Laphygma exempta (eggs) |
|---|---|
| Active compound | % inhibition of development at a concentration of 10 ppm |
| Control | 0% |
| (A) | 20% |
| (13) | 100% |
| (9) | 100% |

EXAMPLE 9

Development-inhibiting action

Test insect: *Ceratitis capitata* (eggs), 20 specimens
Feed: Synthetic feed (carrot powder with yeast powder)
Solvent: 20 parts by weight of acetone
Emulsifier: 5 parts by weight of alkylaryl polyglycol ether To produce a suitable preparation of active compound, 4 parts by weight of active compound were mixed with the stated amount of solvent, emulsifier and sufficient water to produce a 1% strength mixture which was diluted with water to the desired concentration.

The eggs of the test insects were placed on a dish with synthetic feed, into which the selected concentration of the active compound mixture was incorporated so that the stated amount of active compound in ppm (parts per million) was obtained. The development was observed until the flies slipped.

As a control, synthetic feed mixed only with solvent and emulsifier of the stated concentration was presented. The results can be seen from the following table.

TABLE 7
Development-inhibiting action
Ceratitis capitata

| Active compound | % inhibition of development at a concentration of 10 ppm |
|---|---|
| Control | 0% |
| (7) | 100% |
| (8) | 100% |
| (1) | 100% |
| (13) | 100% |
| (9) | 100% |

EXAMPLE 10
Agar plate test mixture. The concentrate was thoroughly mixed, in the stated proportion, with the liquid nutrient medium (which had been cooled to 42° C.) and was then poured into Petri dishes of 9 cm diameter. Control plates to which the preparation had not been added were also set up.

When the nutrient medium had cooled and solidified, the plates were inoculated with the species of organisms stated in the table and incubated at about 21° C.

Evaluation was carried out after 4–10 days, dependent upon the speed of growth of the organisms. When evaluation was carried out the radial growth of the organism on the treated nutrient media was compared with the growth on the control nutrient medium. In the evaluation of the organism growth, the following characteristic values were used:

1 no growth
up to 3 very strong inhibition of growth
up to 5 medium inhibition of growth
up to 7 slight inhibition of growth
9 growth equal to that of untreated control.

The active compounds, the active compound concentrations and the results can be seen from the following table:

TABLE 8
Fungi and bacteria Agar plate test

| Active compound (Concentration = 10 ppm) | Fusarium culmorum | Sclerotinia sclerotiorum | Fusarium nivale | Colletotrichum coffeanum | Rhizoctonia solani | Pythium ultimum | Cochliobolus miyabeanus | Botrytis cinerea | Verticillium alboatrum |
|---|---|---|---|---|---|---|---|---|---|
| (C) | 9 | 9 | 9 | 9 | 9 | 5 | 9 | 9 | 9 |
| (7) | 1 | — | 1 | 3 | 1 | 3 | 1 | 1 | 3 |
| (10) | 1 | 1 | 1 | 1 | 1 | 3 | 1 | 3 | 1 |
| (2) | 1 | 1 | 1 | 1 | — | 1 | 1 | 1 | 1 |
| (13) | 1 | 1 | 1 | 1 | 1 | 1 | 1 | 1 | 1 |
| (6) | 1 | 1 | 5 | 1 | — | — | 5 | — | — |
| (3) | 1 | 3 | 3 | 5 | 1 | — | — | — | — |

| Active compound (Concentration = 10 ppm) | Pyricularia oryzae | Phialophora cinerescens | Helminthosporium gramineum | Mycosphaerella musicola | Phytophthora cactorum | Venturia inaequalis | Pellicularia sasakii | Xanthomonas oryzae | Pseudomonas lachrymans |
|---|---|---|---|---|---|---|---|---|---|
| (C) | 9 | 9 | 5 | 5 | 9 | — | 9 | 9 | — |
| (7) | 1 | 5 | 1 | 1 | 1 | — | 1 | 1 | — |
| (10) | 1 | 1 | 1 | 1 | 1 | — | 1 | — | — |
| (2) | 1 | 1 | 1 | 1 | 1 | — | 1 | 1 | 2 |
| (13) | 1 | 1 | 1 | 1 | 1 | — | 1 | 1 | — |
| (6) | 2 | — | 5 | 3 | 1 | — | 1 | 1 | 1 |
| (3) | 1 | — | 1 | 5 | 1 | — | 5 | — | — |

Nutrient medium used:
20 parts by weight of agar-agar
200 parts by weight of potato decoction
5 parts by weight of malt
15 parts by weight of dextrose
5 parts by weight of peptone
2 parts by weight of disodium hydrogen phosphate
0.3 part by weight of calcium nitrate
Composition of the solvent mixture:
0.19 part by weight of acetone or DMF
0.01 part by weight of emulsifier (alkylaryl polyglycol ether)
1.80 parts by weight of water
Ratio of solvent mixture to nutrient medium:
2 parts by weight of solvent mixture
100 parts by weight of agar nutrient medium
The amount of active compound required for the desired active compound concentration in the nutrient medium was mixed with the stated amount of solvent It will be appreciated that the instant specification and examples are set forth by way of illustration and not limitation, and that various modifications and changes may be made without departing from the spirit and scope of the present invention.

What we claim is:
1. A 2-anilino-3,5-dinitrobenzotrifluoride of the formula

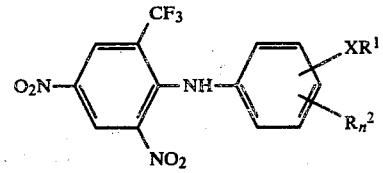

in which

X is O, S, SO or SO$_2$, n is 1, 2, 3 or 4,

R$^1$ is halo-C$_{1-4}$-alkyl, halo-C$_{1-4}$-alkoxy-C$_{1-4}$-alkyl, halo-C$_{1-4}$-alkylphenyl, halo-C$_{1-4}$-alkoxyphenyl, halo-C$_{1-4}$-alkylmercapto-phenyl or halo-C$_{1-4}$-alkylsulphonyl, and R$^2$ each independently is hydrogen, halogen, cyano, C$_{1-4}$-alkyl, halo-C$_{1-4}$-alkyl or halo-C$_{1-4}$-alkoxy-C$_{1-4}$-alkyl, or XR$^1$ and R$^2$, when in the ortho-position relative to one another, together with the two adjacent carbon atoms of the phenyl nucleus, form an optionally halogen-substituted dioxanyl ring, or provided X represents S, SO or SO$_2$, R$^1$ can represent unsubstituted C$_{1-4}$-alkyl in addition to the aforementioned radicals.

2. A compound according to claim 1, in which

X is O, S or SO$_2$,

R$^1$ is alkyl with 1 to 4 carbon atoms, haloalkyl with 1 to 4 carbon atoms, phenyl, chlorophenyl or trifluoromethylsulphonylphenyl, R$^2$ each independently is hydrogen, halogen or trifluoromethyl, and n is 1 or 2, or X-R$^1$ and R$^2$ form a 1,3-dioxane ring which is substituted by fluorine and fused to the phenyl nucleus.

3. A compound according to claim 2, in which

R$^1$ is methyl, ethyl, trifluoromethyl, phenyl, chlorophenyl or trifluoromethylsulphonylphenyl, R$^2$ is hydrogen, chlorine or trifluoromethyl, and n is 1, or X-R$^1$ and R$^2$ form a 1,3-dioxane ring which is substituted by fluorine and fused to the phenyl nucleus.

4. A compound according to claim 1, wherein such compound is 2-[(2,2,4,4- tetrafluorobenzo-1,3-dioxanyl6)-amino]-3,5-dinitro-benzotrifluoride of the formula

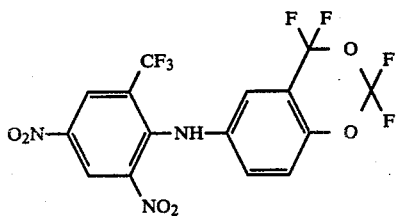

5. A compound according to claim 1, wherein such compound is 2-(4-trifluoromethylthio-anilino)-3,5-dinitro-benzotrifluoride of the formula

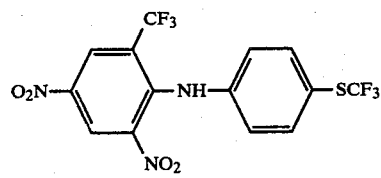

6. A compound according to claim 1, wherein such compound is 2-(2-chloro-4-trifluoromethoxy-anilino)-3,5-dinitrobenzotrifluoride of the formula

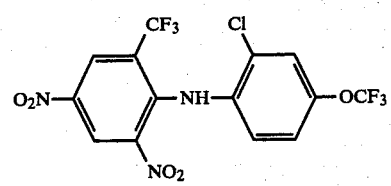

7. A compound according to claim 1, wherein such compound is 2-(2-chloro-4-trifluoromethylthio-anilino)-3,5-dinitrobenzotrifluoride of the formula

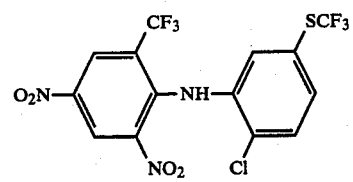

8. A compound according to claim 1, wherein such compound is 2-(3-trifluoromethoxy-anilino)-3,5-dinitrobenzotrifluoride of the formula

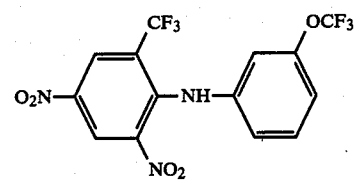

9. An arthropodicidal, nematicidal, fungicidal or bactericidal composition containing as active ingredient an arthropodicidally, nematicidally, fungicidally or bactericidally effective amount of a compound according to claim 1 in admixture with a diluent.

10. A method of combating arthropods, nematrodes, fungi or bacteria, which comprises applying to the arthropods, nematodes, fungi or bacteria, or to a habitat thereof, an arthropodicidally, nematricidally, fungicidally or bactericidally effective amount of a compound according to claim 1.

11. The method according to claim 10, in which said compound is

2-[(2,2,4,4,-tetrafluorobenzo-1,3-dioxanyl-6)-amino]-3,5-dinitro-benzotrifluoride, 2-(4-trifluoromethylthio-anilinol)-3,5-dinitrobenzotrifluoride, 2-(2-chloro-4-trifluoromethoxy-anilino)-3,5-dinitrobenzotrifluoride, 2-(2-chloro-4-trifluoromethylthio-anilino)-3,5-dinitrobenzotrifluoride or 2-(3-trifluoromethoxy-anilino)-3,5-dinitro-benzotrifluoride.

12. A compound of the formula

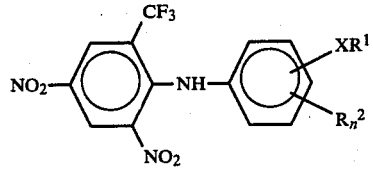

wherein

X is O or S,

R$^1$ is haloalkyl,

R$^2$ is hydrogen or halogen, and n=1, 2, 3 or 4.

13. A composition for the control of mites comprising a mitricidally effective amount of a compound of claim 12 in admixture with a diluent.

14. A method of combating mites, which comprise applying to the mites, or to a habitat thereof, a miticidally effective amount of a compound according to claim 12.

* * * * *